United States Patent
Plowe et al.

(10) Patent No.: US 9,101,387 B2
(45) Date of Patent: Aug. 11, 2015

(54) DIRECTIONAL ROTATIONAL ATHERECTOMY DEVICE WITH OFFSET SPINNING ABRASIVE ELEMENT

(75) Inventors: Charles A. Plowe, Hugo, MN (US);
Jesse C. Darley, Madison, WI (US);
David C. Franchino, Madison, WI (US);
Matthew D. Cambronne, Mounds View, MN (US); Jody Rivers, Elk River, MN (US); Cassandra A. Piippo, Hugo, MN (US); Robert E. Kohler, Lake Elmo, MN (US)

(73) Assignee: Cardiovascular Systems, Inc., St. Paul, MN (US)

( * ) Notice: Subject to any disclaimer, the term of this patent is extended or adjusted under 35 U.S.C. 154(b) by 947 days.

(21) Appl. No.: 12/465,807

(22) Filed: May 14, 2009

(65) Prior Publication Data
US 2010/0121361 A1    May 13, 2010

Related U.S. Application Data

(60) Provisional application No. 61/058,958, filed on Jun. 5, 2008.

(51) Int. Cl.
*A61B 17/22*      (2006.01)
*A61B 17/3207*    (2006.01)
*A61B 17/32*      (2006.01)

(52) U.S. Cl.
CPC ............ *A61B 17/320758* (2013.01); *A61B 2017/320004* (2013.01); *A61B 2017/320766* (2013.01); *Y10T 29/49863* (2015.01)

(58) Field of Classification Search
CPC ......... A61B 2017/320766; A61B 17/320758; A61B 2017/320004; Y10T 29/49863
USPC ............... 606/159, 200, 167, 170, 174
See application file for complete search history.

(56) References Cited

U.S. PATENT DOCUMENTS

| | | | |
|---|---|---|---|
| 4,966,604 A | 10/1990 | Reiss | |
| 5,087,265 A | 2/1992 | Summers | |
| 5,100,424 A | 3/1992 | Jang et al. | |
| 5,100,425 A | 3/1992 | Fischell et al. | |
| 5,312,427 A | 5/1994 | Shturman | |
| 5,314,438 A | 5/1994 | Shturman | |
| 5,356,418 A | 10/1994 | Shturman | |
| 5,360,432 A * | 11/1994 | Shturman | 606/159 |
| 5,402,790 A | 4/1995 | Jang et al. | |
| 5,441,510 A | 8/1995 | Simpson et al. | |
| 5,507,292 A | 4/1996 | Jang et al. | |

(Continued)

FOREIGN PATENT DOCUMENTS

| | | |
|---|---|---|
| JP | 2001-513692 | 9/2001 |
| JP | 2003290239 | 10/2003 |

(Continued)

*Primary Examiner* — Kathleen Holwerda
*Assistant Examiner* — Sarah Simpson
(74) *Attorney, Agent, or Firm* — Winthrop & Weinstine, P.A.

(57) ABSTRACT

The invention provides a rotational atherectomy system, device and method comprising a flexible, elongated, rotatable drive shaft with a pre-curved abrasive section disposed within a catheter that deforms the abrasive section to a substantially straight profile and, when the abrasive section is moved distally out of the catheter, the abrasive section resumes its pre-curved profile. Directional ablation is achieved by rotation of the drive shaft along its pre-curved axis as the abrasive section is urged against a portion of the lumen wall.

20 Claims, 6 Drawing Sheets

(56) References Cited

U.S. PATENT DOCUMENTS

| | | |
|---|---|---|
| 5,554,163 A * | 9/1996 | Shturman ............... 606/159 |
| 5,569,276 A | 10/1996 | Jang et al. |
| 5,843,103 A | 12/1998 | Wulfman |
| 5,895,397 A | 4/1999 | Jang et al. |
| 5,895,402 A | 4/1999 | Hundertmark et al. |
| 5,897,566 A | 4/1999 | Shturman et al. |
| 5,941,869 A | 8/1999 | Patterson et al. |
| 6,022,362 A | 2/2000 | Lee et al. |
| 6,027,460 A | 2/2000 | Shturman |
| 6,113,613 A | 9/2000 | Spaulding |
| 6,113,615 A | 9/2000 | Wulfman |
| 6,132,444 A | 10/2000 | Shturman et al. |
| 6,299,623 B1 | 10/2001 | Wulfman |
| 6,319,242 B1 * | 11/2001 | Patterson et al. ............ 604/508 |
| 6,322,572 B1 | 11/2001 | Lee |
| 6,331,166 B1 | 12/2001 | Burbank et al. |
| 6,423,081 B1 | 7/2002 | Lee et al. |
| 6,440,147 B1 | 8/2002 | Lee et al. |
| 6,451,036 B1 | 9/2002 | Heitzmann et al. |
| 6,494,890 B1 | 12/2002 | Shturman et al. |
| 6,503,261 B1 * | 1/2003 | Bruneau et al. ............... 606/159 |
| 6,508,773 B2 | 1/2003 | Burbank et al. |
| 6,638,288 B1 | 10/2003 | Shturman et al. |
| 6,702,831 B2 | 3/2004 | Lee et al. |
| 6,764,495 B2 | 7/2004 | Lee et al. |
| 6,849,080 B2 | 2/2005 | Lee et al. |
| 6,863,676 B2 | 3/2005 | Lee et al. |
| 6,929,633 B2 | 8/2005 | Evans et al. |
| 7,037,316 B2 | 5/2006 | McGuckin, Jr. et al. |
| 7,192,430 B2 | 3/2007 | Truckai et al. |
| 7,303,531 B2 | 12/2007 | Lee et al. |
| 7,329,267 B2 | 2/2008 | Weber |
| 2003/0060685 A1 | 3/2003 | Houser et al. |
| 2005/0149083 A1 * | 7/2005 | Prudnikov et al. ............ 606/159 |
| 2006/0009785 A1 | 1/2006 | Maitland et al. |
| 2006/0106407 A1 * | 5/2006 | McGuckin et al. ............ 606/159 |
| 2006/0206125 A1 * | 9/2006 | Fogarty et al. ................ 606/159 |
| 2008/0114364 A1 | 5/2008 | Goldin et al. |

FOREIGN PATENT DOCUMENTS

| | | |
|---|---|---|
| WO | WO98/38926 | 9/1998 |
| WO | WO03/043685 | 5/2003 |

\* cited by examiner

DIRECTIONAL ROTATIONAL ATHERECTOMY DEVICE WITH OFFSET SPINNING ABRASIVE ELEMENT

CROSS-REFERENCE TO RELATED APPLICATIONS

The present application claims priority to provisional application No. 61/058,958, filed on Jun. 5, 2008 under the title, "SPINNING OFFSET CUTTER LARGE VESSEL ATHERECTOMY DEVICE", the contents of which are incorporated by reference herein.

BACKGROUND OF THE INVENTION

1. Field of the Invention

The invention relates to devices and methods for removing tissue from body passageways, such as removal of atherosclerotic plaque from arteries, utilizing a rotational atherectomy device.

2. Description of the Related Art

A variety of techniques and instruments have been developed for use in the removal or repair of tissue in arteries and similar body passageways. A frequent objective of such techniques and instruments is the removal of atherosclerotic plaques in a patient's arteries. Atherosclerosis is characterized by the buildup of fatty deposits (atheromas) in the intimal layer (under the endothelium) of a patient's blood vessels. Very often over time, what initially is deposited as relatively soft, cholesterol-rich atheromatous material hardens into a calcified atherosclerotic plaque. Such atheromas restrict the flow of blood, and therefore often are referred to as stenotic lesions or stenoses, the blocking material being referred to as stenotic material. If left untreated, such stenoses can cause angina, hypertension, myocardial infarction, strokes and the like.

Rotational atherectomy procedures have become a common technique for removing such stenotic material. Such procedures are used most frequently to initiate the opening of calcified lesions in coronary arteries. Most often the rotational atherectomy procedure is not used alone, but is followed by a balloon angioplasty procedure, which, in turn, is very frequently followed by placement of a stent to assist in maintaining patency of the opened artery. For non-calcified lesions, balloon angioplasty most often is used alone to open the artery, and stents often are placed to maintain patentcy of the opened artery. Studies have shown, however, that a significant percentage of patients who have undergone balloon angioplasty and had a stent placed in an artery experience stent restenosis—i.e., blockage of the stent which most frequently develops over a period of time as a result of excessive growth of scar tissue within the stent. In such situations an atherectomy procedure is the preferred procedure to remove the excessive scar tissue from the stent (balloon angioplasty being not very effective within the stent), thereby restoring the patentcy of the artery.

Several kinds of rotational atherectomy devices have been developed for attempting to remove stenotic material. In one type of device, such as that shown in U.S. Pat. No. 4,990,134 (Auth), a concentrically shaped ellipsoidal burr covered with an abrasive abrading material such as diamond particles is carried at the distal end of a flexible drive shaft. The burr is rotated at high speeds (typically, e.g., in the range of about 150,000-190,000 rpm) while it is advanced across the stenosis. As the burr is removing stenotic tissue, however, it blocks blood flow. Once the burr has been advanced across the stenosis, the artery will have been opened to a diameter equal to or only slightly larger than the maximum outer diameter of the burr. Frequently, since the burr is of a fixed resting diameter, more than one size burr must be utilized to open an artery to the desired diameter.

U.S. Pat. No. 5,681,336 (Clement) provides an eccentric tissue removing burr with a coating of abrasive particles secured to a portion of its outer surface by a suitable binding material. This construction is limited, however because, as Clement explains at Col. 3, lines 53-55, that the asymmetrical burr is rotated at "lower speeds than are used with high speed ablation devices, to compensate for heat or imbalance." That is, given both the size and mass of the solid burr, it is infeasible to rotate the burr at the high speeds used during atherectomy procedures, i.e., rotational speeds within the range of about 20,000-200,000 rpm. Essentially, the center of mass offset from the rotational axis of the drive shaft would result in development of significant and undesirable centrifugal force, exerting too much pressure on the wall of the artery and creating too much heat and excessively large particles. As with Auth, the burr size is fixed and may require using more than one size burr to open the subject lumen to the desired diameter.

U.S. Pat. No. 6,132,444 (Shturman) and U.S. Pat. No. 6,494,890 (Shturman) both commonly assigned, disclose, inter alia, an atherectomy device having a drive shaft with an enlarged eccentric section, wherein at least a segment of this enlarged section is covered with an abrasive material. When rotated at high speeds, the abrasive segment is capable of removing stenotic tissue from an artery. The device is capable of opening an artery to a diameter that is larger than the resting diameter of the enlarged eccentric section due, in part, to the orbital rotational motion during high speed operation. The orbital rotational motion is primarily due to the offset of the center of mass of the enlarged eccentric section from the drive shaft's rotational axis. Since the enlarged eccentric section may comprise drive shaft wires that are not bound together, the enlarged eccentric section of the drive shaft may flex during placement within the stenosis or during high speed operation. This flexion allows for a larger diameter opening during high speed operation, but may also provide less control than desired over the diameter of the artery actually abraded. The disclosure of U.S. Pat. Nos. 6,132,444 and 6,494,890 are each hereby incorporated by reference in their entirety.

Other techniques and devices have been proposed to generate a rotational sweeping diameter that is greater than the resting diameter of the abrasive section. Generally, these devices include a pre-bent guide wire that will, when placed within the lumen of a rotational drive shaft, create a bend in the drive shaft at the abrasive region. When the guide wire is removed, the drive shaft returns to its normal uncurved and substantially linear shape. Such an arrangement will, when the pre-bent guide wire is in place, create a sweeping diameter for the abrasive region of the drive shaft that is greater than its resting diameter. Examples of such pre-bent guide wire proposals include U.S. Pat. Nos. 5,312,427, 5,356,418, 5,554, 163 all to Shturman and commonly assigned with the present application, the disclosure of each being incorporated herein by reference insofar as they disclose a drive shaft is urged into a curvilinear profile by virtue of the presence of the curved guide wire within the drive shaft's lumen. Other examples include U.S. Pat. No. 5,548,843 to Wulfman and U.S. Pat. No. 6,156,046 to Passafaro.

The pre-curved guide wire designs each require the guide wire to be in place within the lumen of the drive shaft to create the desired bending of the drive shaft and abrasive region which may hamper flexibility of the drive shaft during high-speed rotation. Further, the pre-curved guide wire approach may find difficulty in traversing the often tortuous vasculature enroute to the stenosis of interest. Moreover, the pre-curved guide wire devices are not designed for focused directional ablation.

Thus, it would be highly advantageous to provide an atherectomy system, device and method that is substantially linear upon entry into the patient's vasculature but at the same time allows for directional abrading and/or cutting within a lumen as well as the possibility of expansion of the sweeping diameter of the spinning drive shaft's abrasive region based, at least in part, upon pre-bending of the drive shaft itself, not the guide wire as previously proposed.

The present invention addresses, inter alia, these needs.

BRIEF SUMMARY OF THE INVENTION

The invention provides a rotational atherectomy system, device and method comprising a flexible, elongated, rotatable drive shaft with a pre-curved abrasive section disposed within a catheter that deforms the curved abrasive section to a substantially straight profile and, when the abrasive section is moved distally out of the catheter, the abrasive section resumes its pre-curved profile. Directional ablation is achieved by rotation, i.e., spinning, of the drive shaft and abrasive element along at least one of its pre-curved directional axes of rotation as the abrasive section is urged against a portion of the lumen wall.

An object of the invention is to provide a rotational atherectomy device having a drive shaft with a pre-curved abrasive section for directional ablation.

Another object of the invention is to provide a rotational atherectomy device having a catheter that receives the pre-curved drive shaft, at least partially straightening the pre-curved section of the drive shaft when received within the catheter.

Another object of the invention is to provide a rotational atherectomy device comprising an abrasive element and/or cutting element at the midpoint and/or peak of the pre-curved section.

Another object of the invention is to provide a rotational atherectomy device comprising a pre-curved section with an abrasive zone and a cutting zone to allow achieving cutting and grinding/abrasion independently and within the same procedure.

Another object of the invention is to provide a rotational atherectomy device for directional ablation comprising a pre-curved drive shaft having at least one abrasive section thereon, wherein the operator controls which abrasive section, e.g., a grinding element or a cutting element, is exposed to the target tissue.

Another object of the invention is to provide a rotational atherectomy device for directional ablation comprising a pre-curved drive shaft with at least one abrasive section thereon, wherein the drive shaft is capable of bi-directional rotation and wherein rotation in one direction provides a less aggressive ablation than does rotation in the other direction.

Another object of the invention is to provide a rotational atherectomy device with a drive shaft capable of bi-directional rotation, wherein the abrasive element grinds in one rotational direction and cuts in the other rotational direction.

Another object of the invention is to provide a rotational atherectomy device with a pre-curved region of the drive shaft and comprising an eccentric enlarged section of the drive shaft within the pre-curved region to induce orbital spinning motion by moving the center of mass radially off of one of several axes of rotation of the directional element of the drive shaft for directional ablation.

Another object of the invention is to provide a rotational atherectomy device with a pre-curved region of the drive shaft and comprising a concentric enlarged abrasive section of the drive shaft within the pre-curved region, wherein the center of mass is substantially co-linear with one of several axes of rotation of the pre-curved section of the drive shaft for directional ablation.

Another object of the invention is to provide a rotational atherectomy device with a pre-curved region of the drive shaft and comprising an eccentric at least partially solid crown attached to the drive shaft within the pre-curved region to induce orbital motion by moving the center of mass radially off of the relevant axis of rotation of the pre-curved section of the drive shaft for directional ablation.

Another object of the invention is to provide a rotational atherectomy device with a pre-curved region of the drive shaft and comprising an abrasive burr attached to the drive shaft within the pre-curved region for directional ablation.

Another object of the invention is to provide a rotational atherectomy device with a pre-curved region of the drive shaft and comprising a concentric abrasive burr attached to the drive shaft within the pre-curved region for directional ablation.

Another object of the invention is to provide a rotational atherectomy device with a pre-curved region of the drive shaft and comprising an eccentric abrasive burr attached to the drive shaft within the pre-curved region to induce orbital motion by moving the center of mass radially off of the axis of rotation of the drive shaft for directional ablation.

Another object of the invention is to provide a rotational atherectomy device with a pre-curved region of the drive shaft and comprising an abrasive annular ring attached to the drive shaft within the pre-curved region for directional ablation.

Another object of the invention is to provide a rotational atherectomy device comprising user control of the magnitude of radial expansion of the pre-curved section.

Another object of the invention is to provide a rotational atherectomy device for directional ablation comprising a pre-curved drive shaft with abrasive section thereon, wherein the curvilinear profile characteristics, e.g., height and length, of the pre-curved section are controlled by the operator.

Another object of the invention is to provide a system and methods to achieve, inter alia, the above objectives.

The figures and the detailed description which follow more particularly exemplify these and other embodiments of the invention.

BRIEF DESCRIPTION OF THE DRAWINGS

The invention may be more completely understood in consideration of the following detailed description of various embodiments of the invention in connection with the accompanying drawings, which are as follows.

DETAILED DESCRIPTION OF THE INVENTION, INCLUDING THE BEST MODE

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention.

Figure 1:
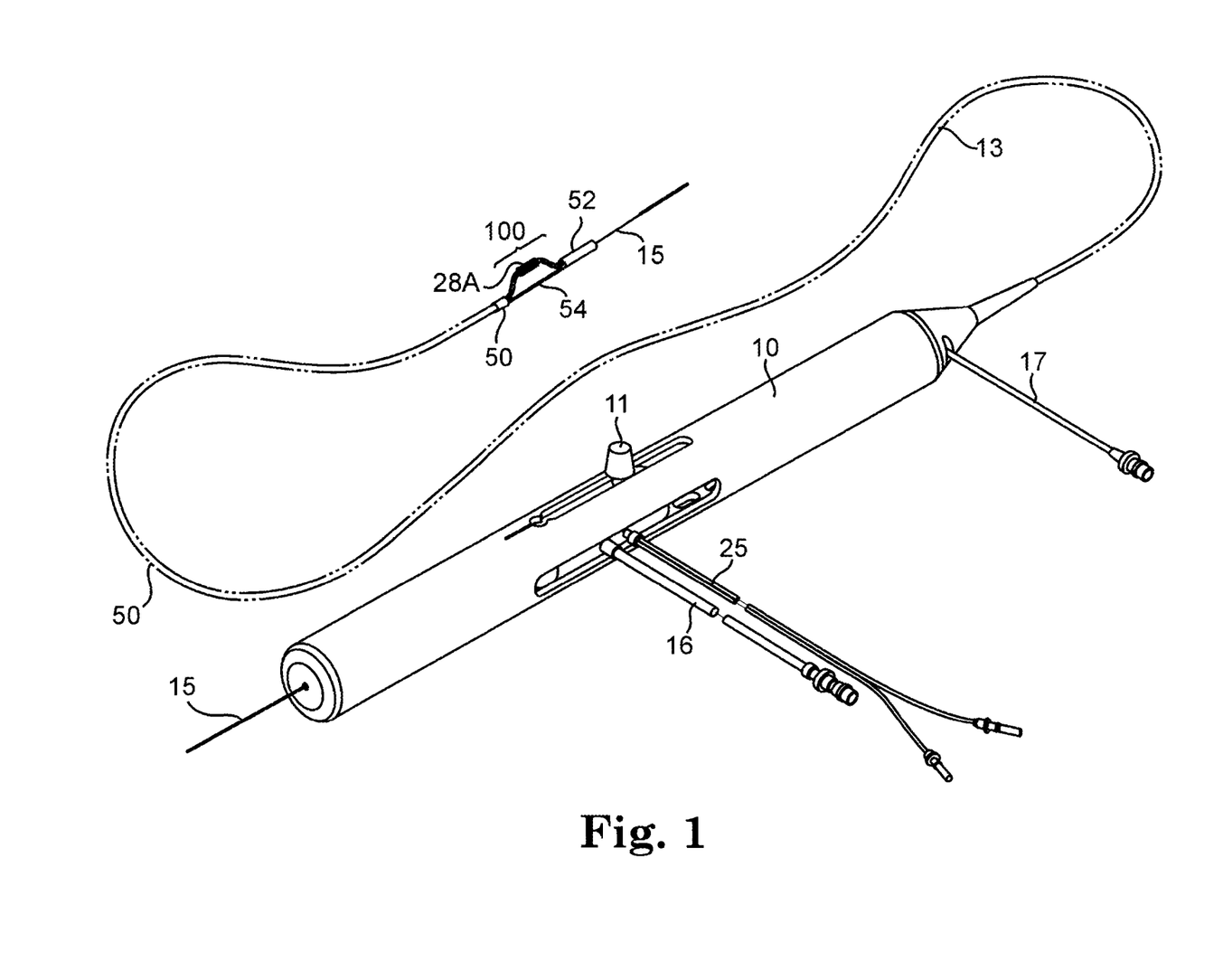
FIG. 1 is a perspective view of one embodiment of the present invention.

FIG. 1 illustrates one embodiment of a rotational atherectomy system and device of the present invention. The system includes a handle portion 10, an elongated, flexible drive shaft 20 having a pre-curved section 100 which further comprises an abrasive section or element 28, illustrated without limitation as a concentric atherectomy crown 28A, which is attached to drive shaft 20 within pre-curved section 100. The drive shaft 20 may be, as is well known in the art, constructed from helically coiled wire(s). Drive shaft also comprises a proximal section 20p, at least part of which is disposed within the inner tube proximal section and a distal section 20d, at least part of which is disposed within the inner tube distal section 52 with pre-curved section 100 disposed therebetween. Proximal section 20p and distal section 20d of drive shaft may comprise a common rotational axis in certain embodiments, though this is not a necessary condition to achieve the inventive objectives herein; as illustrated in FIG. 1, proximal section 20p and distal section 20d share a common rotational axis. Further, pre-curved section 100 is illustrated as radially extended from the proximal section 20p and distal section 20d to achieve directional biasing for the abrasive section 28. Distal section 20d of drive shaft terminates within inner tube distal section 52 in this embodiment at a bearing means (not shown) well known to those skilled in the art and which allows the drive shaft 20 to rotate thereby. Further, bearing means may provide a distal stop for drive shaft 20 in certain embodiments, enabling the operator to apply pressure along the drive shaft 20 in a distal direction, causing the pre-curved section 100 to bow radially outwardly.

Inner tube comprises a proximal section 50, a distal section 52 and a spanning section 54 therebetween as will be discussed further infra. The proximal and distal sections 50, 52 of the inner tube comprise a lumen therethrough, wherein at least portions of the drive shaft 20 may be disposed as well as portions of the guide wire 15. Pre-curved section 100 is illustrated as adjacent spanning section 54 of inner tube and further in an extended, i.e., deployed, position which, as described infra, comprises radial biasing of the abrasive section 28 attached thereto. Inner tube sections 50, 52 and 54 and the drive shaft 20 may be slidingly received within elongated outer catheter 13 extending distally from the handle portion 10.

Thus, the outer catheter 13 comprises a lumen in which the lengths of inner tube 50, 52, 54, drive shaft 20 and guide wire 15 may be disposed, wherein catheter 13 may be slidable, i.e., advanced or withdrawn axially, independent of inner tube, drive shaft and guide wire. The drive shaft 20 may also contain an inner lumen that permits, inter alia, the drive shaft 20 to be advanced and rotated over a guide wire 15 which, when inserted therethrough, may deform the pre-curved section 100 to a substantially straightened linear profile. However, the preferred embodiment comprises the guide wire 15 disposed slidingly within catheter 13 but external to the drive shaft 20 and within inner tube's lumen wherein the guide wire is independently advanceable and withdrawable. A fluid supply line 17 may be provided for introducing a cooling and lubricating solution (typically saline or another biocompatible fluid) into the catheter 13 wherein fluid supply line is operatively connected with catheter. In certain embodiments warming and/or cooling biocompatible fluid may be introduced and/or urged into the catheter 13 via fluid supply line. Generally, abrasive section 28, e.g., concentric cylindrical crown 28A, comprises an abrasive coating at least partially thereon to facilitate tissue removal. Alternatively, the surface of abrasive section 28, e.g., concentric cylindrical crown 28A, may be at least partially roughened and/or etched to facilitate tissue removal. Additional embodiments of the abrasive section 28 will be discussed further infra.

The handle 10 desirably contains a turbine (or similar rotational drive mechanism) for rotating the drive shaft 20 at high speeds. The handle 10 typically may be connected to a power source, such as compressed air delivered through a tube 16. A pair of fiber optic cables 25 may also be provided for monitoring the speed of rotation of the turbine and drive shaft 20 (details regarding such handles and associated instrumentation are well known in the industry. The handle 10 also desirably includes a control knob 11 for advancing and retracting the turbine and drive shaft 20 with respect to the catheter 13 and the body of the handle 10.

Figure 2:
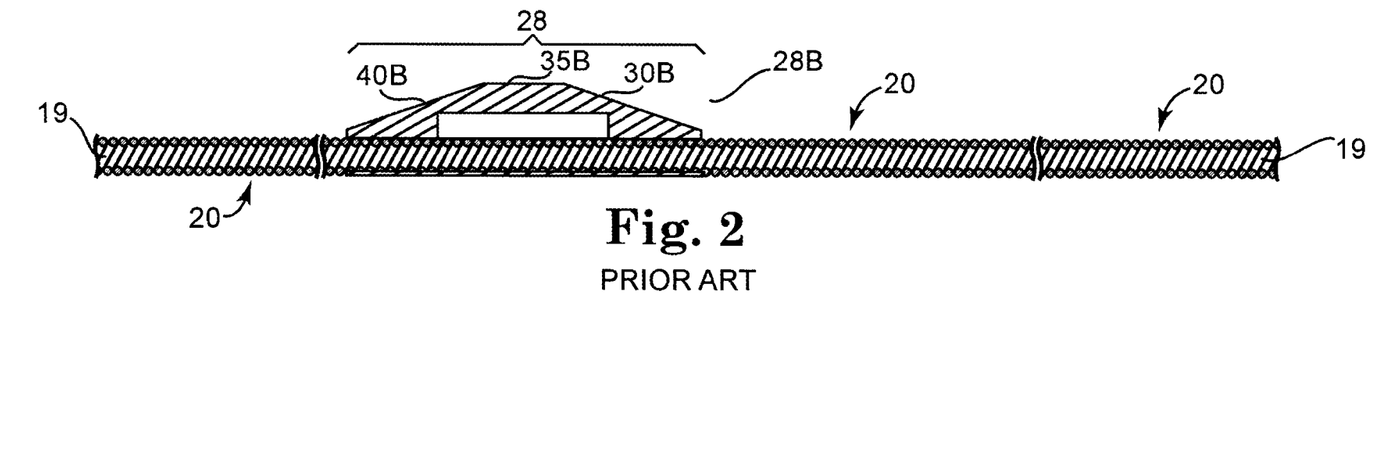
FIG. 2 is a cutaway side view of one embodiment of a prior art device.
Figure 3:
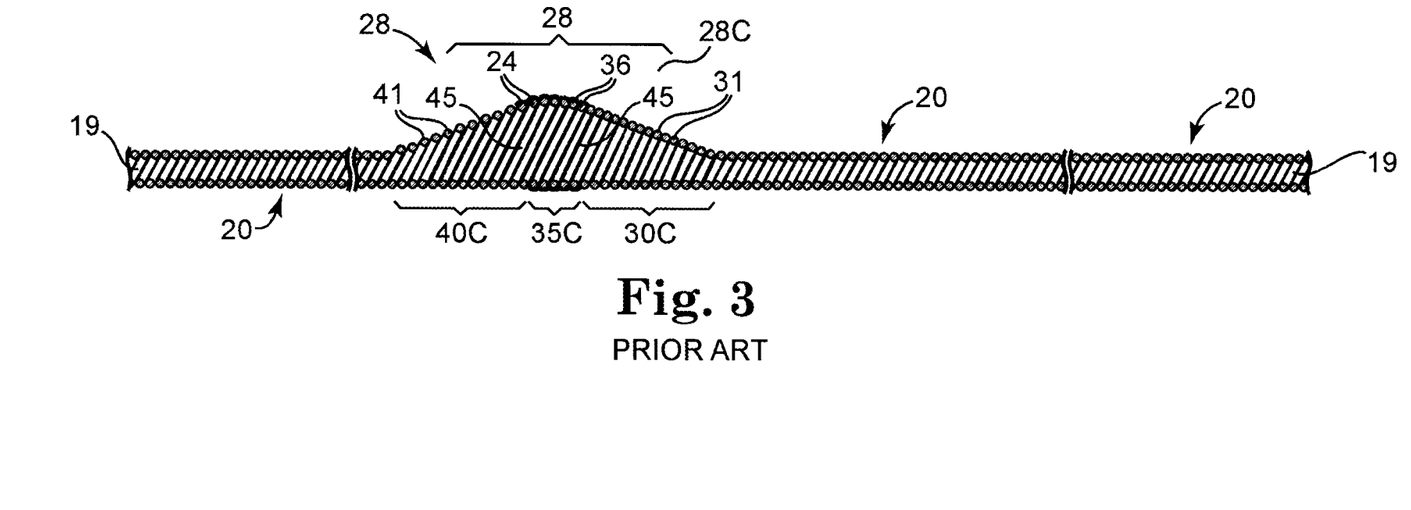
FIG. 3 is a cutaway side view of one embodiment a prior art device.

With reference now to FIGS. 2 and 3, two embodiments of known systems comprising abrasive sections 28 for high-speed rotational atherectomy devices and procedures are illustrated. FIG. 2 provides a cross-sectional view of a rotational drive shaft 20 with lumen 19 therethrough. The device is illustrated as substantially linear and without a guide wire disposed within drive shaft lumen 19 or catheter disposed therearound. Further, eccentric and at least partially solid crown 28B is illustrated as comprising the abrasive section 28. Eccentric solid crown 28B comprises proximal 30B, intermediate 35B and distal 40B portions. An abrasive (not shown) may be coated upon one or more of the proximal 30B, intermediate 35B and distal 40B portions as is well known to those skilled in the art.

FIG. 3 illustrates another known high-speed rotational embodiment, wherein the drive shaft 20 with abrasive section 28 comprising an eccentric enlarged section 28C of drive shaft 20 with lumen 19 therethrough for receiving guide wire (not shown). The drive shaft 20 is, as is the known FIG. 2 device, substantially linear without guide wire disposed within lumen 19 and/or without a catheter disposed therearound.

Drive shaft 20 is comprised of one or more helically wound wires 18 which define a guide wire lumen 19 and a hollow cavity 45 within the enlarged diameter section 28C. Enlarged diameter section 28C comprises proximal 30C, intermediate 35C and distal 40C portions. Wire turns 31 of the proximal portion 30 of the eccentric enlarged diameter section 28C preferably have diameters that progressively increase distally at a generally constant rate, thereby forming generally the shape of a cone. Wire turns 41 of the distal portion 40 preferably have diameters that progressively decrease distally at a generally constant rate, thereby forming generally the shape of a cone. Wire turns 36 of the intermediate portion 35C are provided with gradually changing diameters to provide a generally convex outer surface which is shaped to provide a smooth transition between the proximal and distal conical portions of the enlarged diameter section 28C of the drive shaft 20.

At least part of the abrasive section 28, illustrated as eccentric enlarged diameter section 28C (preferably the intermediate portion 35) may comprise a coating 36 of an abrasive material 24 to define a tissue removing segment of the drive shaft 20 as is well known in the art and which will be discussed further infra.

Figure 4:
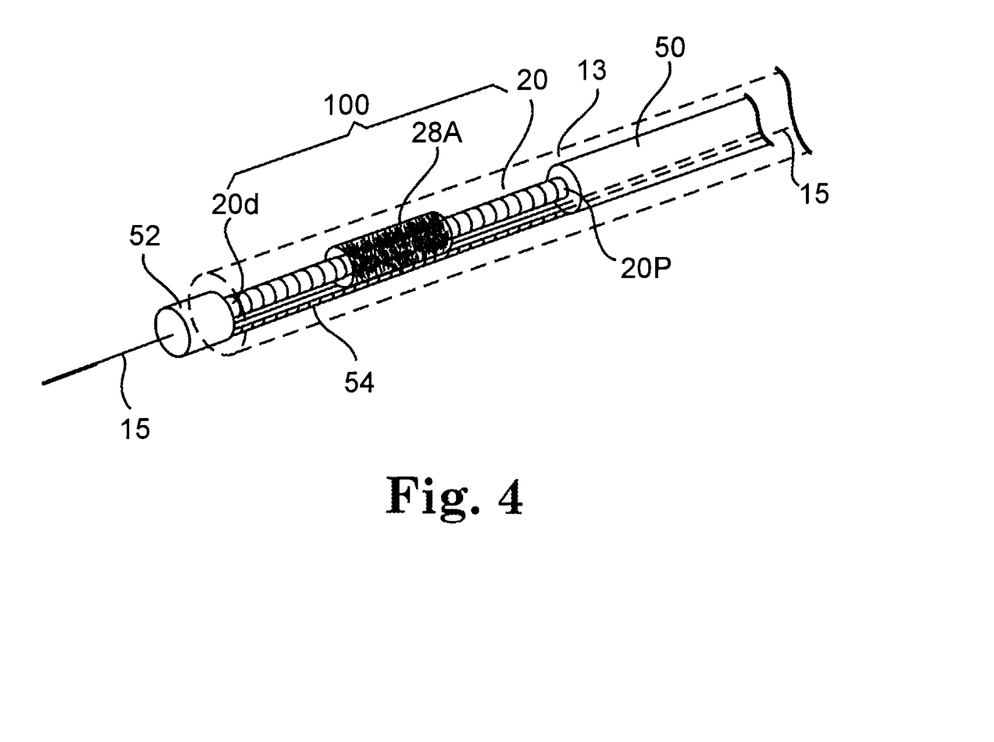
FIG. 4 is a perspective and partial cutaway view of one embodiment of the present invention.

The devices of FIGS. 3 and 4 are intended to abrade the entire inner surface of a lumen during high-speed atherectomy procedures. As a consequence, they are unable to provide directional ablation to target tissues along a part of the subject lumen while leaving the non-target, i.e., healthy, tissue untouched.

Figure 5:
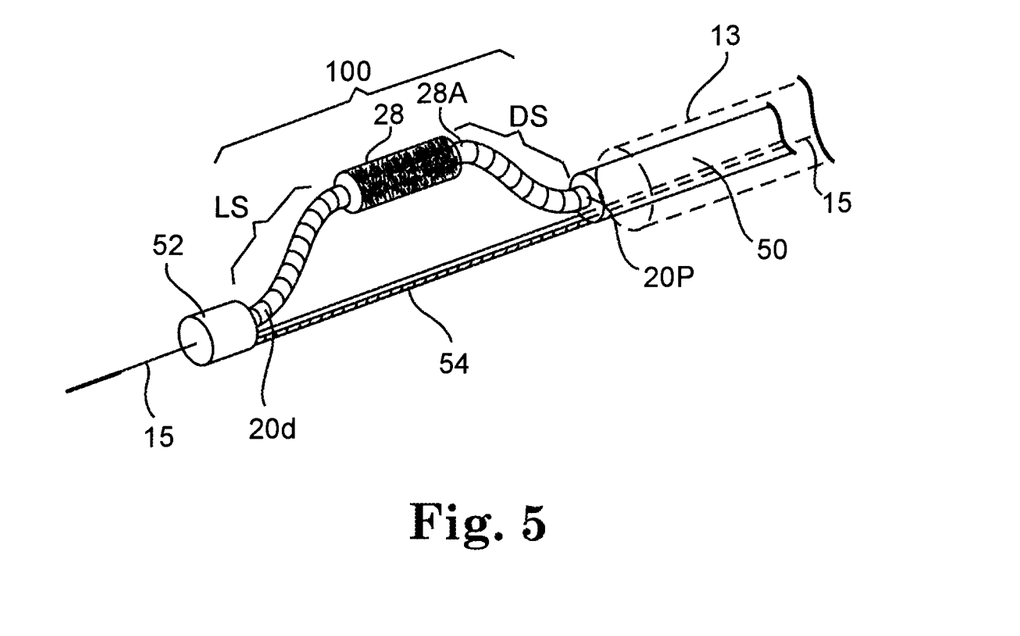
FIG. 5 is a perspective and partial cutaway view of one embodiment of the present invention.

Turning now to FIGS. 4 and 5, one embodiment of a pre-curved drive shaft 20 of the present invention are illustrated. This embodiment comprises a pre-curved section 100 having a curvilinear profile and which further comprises an abrasive section 28 formed and/or operatively disposed on the drive shaft 20 at least partly at the peak P of the pre-curved section 100. Preferably, pre-curved section 100 is formed on the drive shaft 20 proximal to distal portion of drive shaft $20_d$. Abrasive section 28 is illustrated as comprising a concentric abrasive crown 28A thereon. FIG. 4 provides the pre-curved section 100 and abrasive element 28A in straightened deformed profile by virtue of the pre-curved section 100 being received within catheter 13. FIG. 5 illustrates the pre-curved section 100 being allowed to return to its undeformed, curvilinear and pre-curved profile as either catheter 13 has been withdrawn proximally, or drive shaft 20 has been advanced distally, or by a combination of these movements.

Figure 6:
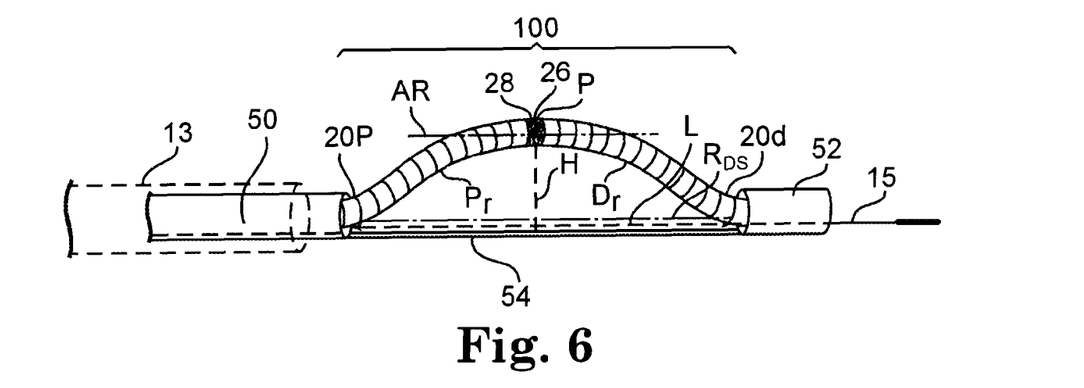
FIG. 6 is a partial cutaway side view of one embodiment of the present invention.
Figure 7:
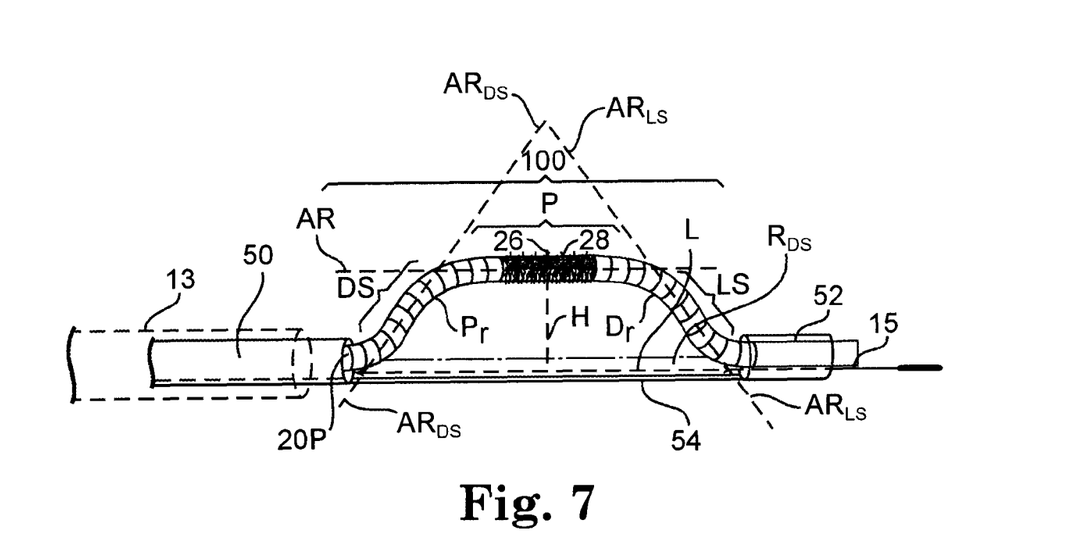
FIG. 7 is a partial cutaway side view of one embodiment of the present invention.

Turning to FIGS. 6 and 7, another embodiment of the present invention is provided wherein abrasive section 28 is illustrated as comprising abrasive coating 26 directly onto the wire turns of the drive shaft 28. For all embodiments, the peak P of pre-curved section 100 may be a substantially discreet point as in FIG. 6 or, as in FIG. 7, a series of substantially linear points wherein peak P may comprise a substantially linear profile. Abrasive section 28 may be formed and/or operatively disposed at least partly at peak P in either embodiment. Moreover, each pre-curved section 100 further comprises a height H and a length L as shown in the Figures. In either embodiment, the drive shaft comprises a rotational axis AR generally at peak P. When the drive shaft is urged to rotate or spin either by operator's hand or motorized means, the peak P and abrasive element 28 tend to concentrically rotate about axis of rotation AR in certain embodiments of the present invention, i.e., without orbital motion wherein the sweeping diameter of the abrasive section 28 is greater than its resting diameter. In other embodiments, discussed infra, peak P and abrasive element 28 may comprise an orbital motion about axis of rotation AR.

The present invention may comprise more than one axis of rotation within pre-curved section 100. By way of example, an axis of rotation may either coincide with peak P or be substantially collinear therewith as in axis of rotation AR. Further rotational axes may be provided along leading (distal) section of pre-curved section LS as illustrated by $AR_{LS}$ or along trailing (proximal) section of pre-curved section DS as illustrated by $AR_{DS}$. The skilled artisan will recognize many additional possible axes of rotation around which the at least one abrasive element 28 may rotate.

In certain embodiments, the curvilinear profile, defined, e.g., by height H and the length L and radius/radii of the pre-curved section 100 may be adapted, and in some embodiments dynamically adaptable as will be further described infra, to the changing geometries of a passageway within a stenosis or body lumen. For example, the height H to length L ratio may preferably be in the range from 0.1:1 to 5:1, though the skilled artisan will recognize that height H to length L ratios greater than 5:1 will certainly have application; each such ratio is within the scope of the present invention.

Moreover, as will be further described herein, the height H and the length L of the pre-curved section 100 may be changed, and controlled, by the operator in certain embodiments of the present invention as the stenosis is progressively abraded away by the present invention. Specifically, the height H may be increased (or decreased) and the length L may be increased (or decreased) depending on the particular needs and the prevailing environment at the time, i.e., the size of the passageway through the stenosis. Further discussion regarding operator control of the curvilinear characteristics of pre-curved section 100 is provided infra.

Pre-curved section 100 further comprises at least one radiused section, preferably two radiused sections, and may further comprise a substantially linear section as shown in FIG. 7 corresponding to peak P, wherein the peak P is substantially linear and substantially parallel with the drive shaft's proximal section and distal section. For example, a proximal radiused section $P_r$ and a distal radiused section $D_r$ may be provided with peak P therebetween. The radiused section(s) may vary in curvature and may, or may not, comprise substantially equivalent curvatures. Orbital motion of the abrasive element 28 may be induced by, inter alia, providing radiused sections that do not have equivalent curvature. Those skilled in the art will recognize the varying radius and/or radii and curvature thereof, height H, length L and profile form of peak P, as well as rotational speed, placement of the at least one abrasive section 28 within pre-curved section 100, among other variables, comprise a plurality of parameters that may form a wide variety of combinations; each such combination is within the scope of the present invention.

It can now be readily seen that the illustrated embodiments in FIGS. 6 and 7 comprise the abrasive section 28, disposed generally at peak P as being radially offset from the rotational axis of the non-curved and substantially linear portions, i.e., proximal and distal sections, of drive shaft $R_{DS}$, such transverse offset being generally defined by height H of precurved section 100. This offset of abrasive section 28 provides a biased directionality that allows focused ablation comprising grinding and/or cutting of target tissue without engaging unwanted tissue. The skilled artisan will recognize that the axes of rotation for proximal section and distal section need not necessarily be substantially collinear as illustrated in the Figures. Alternatively, an offset in the axes of rotation for proximal and distal sections may be advantageous in achieving the desired directionality, exposure of selected abrasive section tool(s), and/or developing an eccentricity of rotation that may lead to orbital motion.

Moreover, those skilled in the art will recognize that providing an abrasive section 28 with an eccentric crown or burr or enlarged drive section, for example, of the drive shaft as described herein will tend to place additional force on the peak P section, or other location within of pre-curved section 100, during rotation which will, in some cases as is well understood in the art, tend to increase the distance of the rotational path of abrasive section 28, i.e., enlarging the swept diameter such that the swept diameter is larger than the abrasive section's resting diameter. Such an arrangement may further induce orbital motion of abrasive section 28 during rotation.

As discussed herein, the abrasive section 28 formed and/or operatively disposed at least partly at peak P, or at other location(s) within pre-curved section 100, may comprise many different forms, each of which are within the scope of the present invention. For example, and without limitation, abrasive section 28 may simply be an abrasive formed on or coated 26 onto the cylindrically-shaped drive shaft 20 as illustrated in FIGS. 6 and 7, wherein abrasive material is coated thereon, specifically diamond dust or the equivalent, or formed thereon by etching or the equivalent, each such technique being well known in the art.

Figure 8:
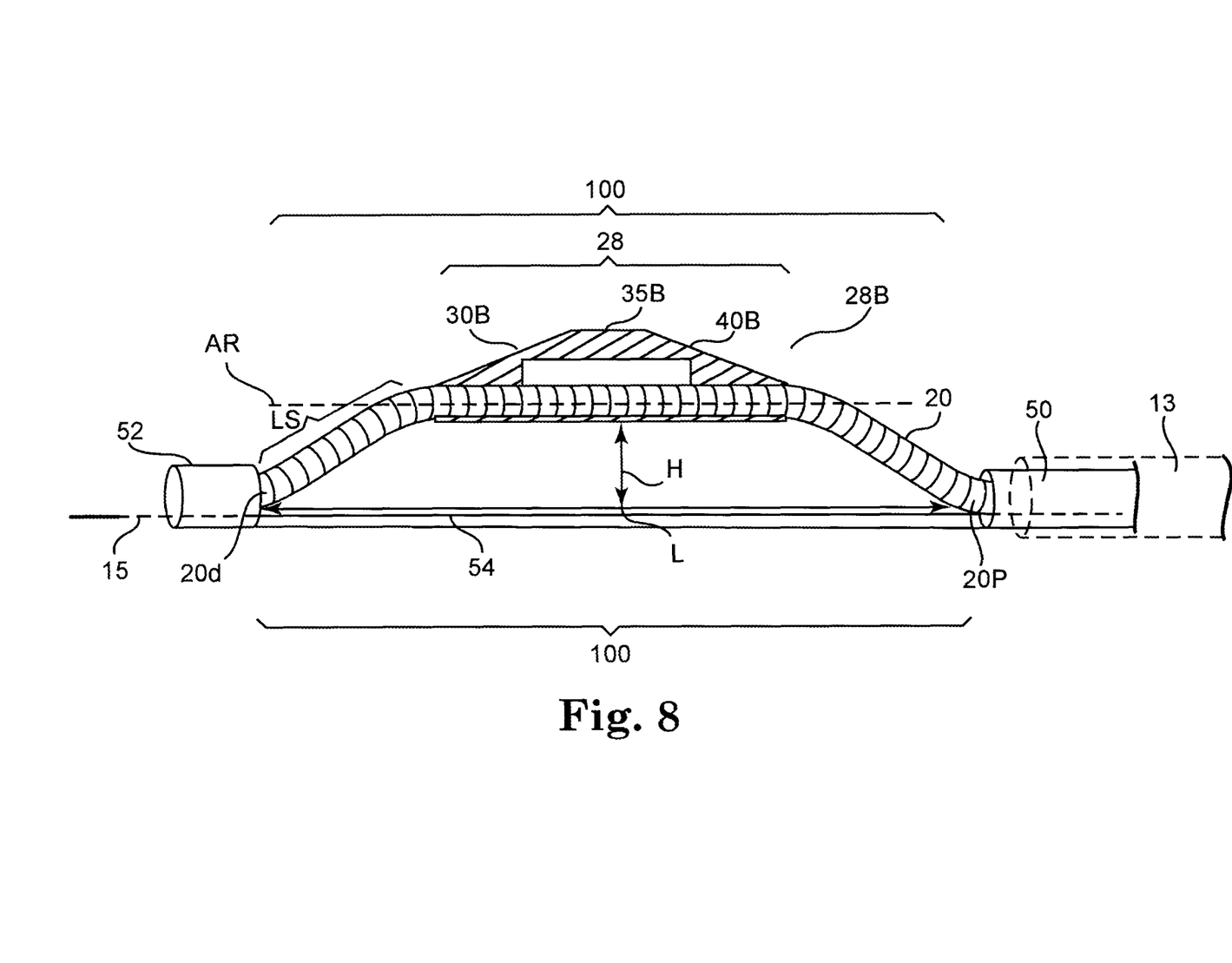
FIG. 8 is a partial cutaway side view of one embodiment of the present invention.

Alternatively, the abrasive section 28 may comprise a concentric burr or an eccentric burr, or a concentric, or an eccentric crown as described in commonly assigned U.S. patent application Ser. No. 11/761,128 the disclosure of which is incorporated herein in its entirety insofar as it describes an eccentric crown attached to the drive shaft 20 and at least partially coated with abrasive. A particular embodiment of an eccentric and at least partially solid crown 28B is shown in FIG. 8. These concentric or eccentric burr and concentric or eccentric crown embodiments of abrasive section 28 may be attached to the drive shaft 20 at the peak of the pre-curved section and/or attached to other regions of the pre-curved section, whether the drive shaft 20 comprises a cylindrical profile at the abrasive section or a concentric or eccentric enlarged diameter section as discussed infra.

Other embodiments of abrasive section 28 may comprise an annular abrasive ring (not shown) as described in commonly assigned U.S. patent application Ser. No. 10/272,164 the disclosure of which is incorporated herein in its entirety insofar as it describes an abrasive section comprising an annular ring or sleeve coated with abrasive, or having an abrasive surface thereon, that is slid over and attached to the drive shaft 20, and which may be attached to the drive shaft 20 at the peak of the pre-curved section and/or attached to other regions of the pre-curved section, whether the drive shaft 20 comprises a cylindrical profile at the abrasive section as illustrated in FIGS. 6 and 7, or a concentric or eccentric enlarged diameter section as discussed infra.

Figure 9:
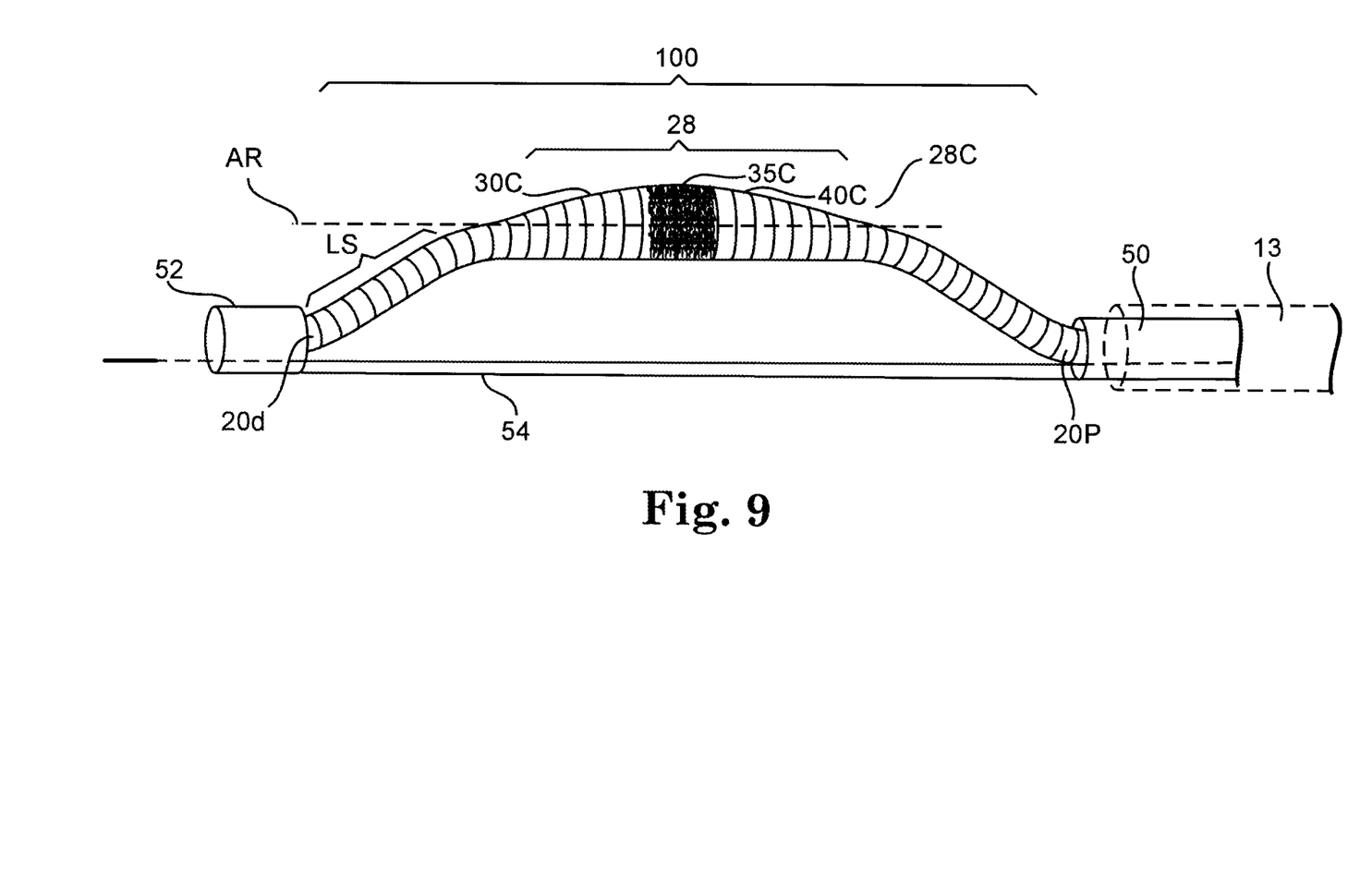
FIG. 9 is a partial cutaway side view of one embodiment of the present invention.

Still more alternatively as illustrated in FIG. 9, the abrasive section 28 of the present invention may comprise an eccentric enlarged section of the drive shaft 28C coated at least partially with abrasive and/or comprising an external abrasive surface, as described in detail in commonly assigned U.S. Pat. No. 6,494,890, the disclosure of which is incorporated herein in its entirety insofar as it describes an abrasive section 28 comprising an eccentric enlarged section of the drive shaft 20 that is coated with an abrasive. Still more alternatively the abrasive section 28 may comprise a concentric enlarged section of the drive shaft coated at least partially with abrasive, as described in detail in commonly assigned U.S. Pat. No. 5,314,438, the disclosure of which is incorporated herein in its entirety insofar as it describes an abrasive section comprising a concentric enlarged section of the drive shaft 20 that is coated with an abrasive and/or comprises an external abrasive surface.

It should be understood that, as used herein, the word "eccentric" is defined herein to mean either a difference in location between the geometric center of the abrasive section 28, in its various alternate embodiments as described herein, and the rotational axis of the drive shaft, or to a difference in location between the center of mass of the eccentric embodiment of abrasive section 28, and in its various alternate embodiments as described herein, and the rotational axis of the drive shaft 20. These parameters at the proper rotational speeds will enable the abrasive section 28 to open a stenosis to a diameter that is greater than the nominal diameter of the abrasive section 28. Moreover, for an eccentric abrasive section 28 having a shape that is not a regular geometric shape, the concept of "geometric center" can be approximated by locating the mid-point of the longest chord which is drawn through the rotational axis of the drive shaft and connects two points on a perimeter of a transverse cross-section taken at a position where the perimeter of the eccentric enlarged diameter section has its maximum length. Moreover, those skilled in the art will recognize that eccentricity as defined may be designed into an abrasive section 28 having a substantially concentric profile, but with one aspect of the profile being more massive than the rest by, e.g., hollowing out a portion of one side of the abrasive section 28 as is illustrated in the partially hollow solid eccentric crown of FIG. 8. Further, eccentric as used to describe the rotational diameter of abrasive section 28 of certain embodiments of the present invention means that the rotational radii are not substantially equivalent around the circumference of the rotational path of abrasive section 28, thus an orbital pathway, i.e., orbital motion, for the abrasive section 28 may be developed.

Moreover, it should also be understood that concentric as used herein, is defined to mean an abrasive section 28 that comprises a center of mass that is on, i.e., collinear with, e.g., the axis of rotation AR of the pre-curved section 100 location to which abrasive section 28 is operatively connected/attached and a profile that is substantially symmetrical. Moreover concentric as used in connection with the rotational diameter of abrasive section 28 of the present invention means that the rotational radii are substantially equivalent around the circumference of the rotational path of abrasive section 28.

In all embodiments of the abrasive section 28, the abrasive 26 may be coated onto various surfaces, or all surfaces, of the various embodiments of abrasive section 28. By way of example, the abrasive material may be any suitable material, such as diamond powder, fused silica, titanium nitride, tungsten carbide, aluminum oxide, boron carbide, or other ceramic materials. The abrasive material may comprise diamond chips (or diamond dust particles) attached and/or coated directly to the surface of abrasive section 28, such attachment may be achieved using well known techniques, such as conventional electroplating or fusion technologies (see, e.g., U.S. Pat. No. 4,018,576). Alternately the abrasive section 28 may comprise an external tissue removing surface which has been roughened to provide a suitable abrasive surface. In yet another variation, the external surface may be etched or cut (e.g., with a laser) to provide small but sharp cutting surfaces. Other similar techniques may also be utilized to provide a suitable tissue removing surface for abrasive section 28.

Alternatively, the drive shaft 20 may rotate in two directions, thus comprising bi-directional rotation, and the at least one abrasive section 28 may comprise a grinding element which grinds stenotic tissue when drive shaft 20 is rotated in the direction wherein the grinding element engages stenotic tissue. Further, the abrasive section 28 may comprise a cutting element on an opposing surface of the grinding element, wherein rotation of the drive shaft in the opposite direction results in the cutting element engaging, and cutting, stenotic tissue. In this manner, the abrasive section 28 may comprise, in one rotational direction, a grinding or abrasive effect, and in the other rotational direction, a cutting effect. Alternatively, the opposing sides of at least one abrasive element 28 may comprise varying abrasive grit sizes, thereby allowing for less grinding in one rotational direction and more grinding in the other rotational direction.

The apparatus and system having been described, the method of formation of the pre-curved section 100 will now be discussed in detail.

The pre-curved section 100 may be fixedly formed or adapted by a variety of techniques, one of which comprises a unique heat setting method. Under this method, initially, the drive shaft 20 is wound using a coil winder as is well known in the art. Next, the entire length of wound drive shaft 20 receives a 200 degree C. heat set for one hour to relax and stabilize the coil dimensions. Treatments of this type are common in spring and coil manufacturing and are intended to pre-relax the wound drive shaft 20 coils. The skilled artisan will recognize additional variations of time and temperature for the pre-relaxation step, each such variation being within the scope of the present invention, thus the particular parameters provided are for illustration only and in no way limit the scope of the present invention.

Next, a mandrel shaped in the desired curved drive shaft form is inserted into the lumen 19 at the distal end of the straight (and pre-relaxed) drive shaft 20. Thus, the drive shaft 20 is forced to take on the shape of the mandrel. The mandrel may be formed of and/or comprise materials well known to those skilled in the art, including, inter alia, stainless steel.

After the mandrel is in place within the drive shaft lumen 19, a local heat treatment is performed on the curved portion of the drive shaft 20 is performed with the mandrel in place using well known techniques. Typical local heat treatment conditions for this step of the method may comprise exposing the curved section with mandrel therein to a heat of 555 degrees C. for 30 minutes, though these particular parameters in no way limit the scope of the invention. To the contrary, those skilled in the art will recognize additional variations of time and temperature for the local heat treatment step, each such variation being within the scope of the present invention. The local heat treatment provides much greater stress relief than the previous pre-relaxation heat treatment step and, in addition, provides the activation energy necessary to relieve even the lower energy dislocation sites within the section of the drive shaft 20 to be curved under the curving process. Dislocations in the drive shaft 20 filars are set such that they promote the bent shape even without aid from the mandrel.

After the local heat treatment is complete, the mandrel is removed and the curved shape is retained by the drive shaft 20 thus forming the pre-curved section 100 of the present invention. Thus, the described technique provides a pre-set and non-dynamically adaptable pre-curved section 100 of fixed height H and length L and adapted curvilinear profile. Alternate method steps may comprise electrolytic polishing of the pre-curved section 100, particularly the portion of the drive shaft 20 that was subjected to the local heat treatment, to remove any oxidation.

Other mechanisms and methods for forming the pre-curved section 100 of the present invention may comprise using shape memory alloy materials and are contemplated under the present invention. One example of a material that can be used for the pre-curved section is a shape memory alloy such as nickel-titanium (NiTi), commonly referred to as Nitinol. Nitinol exhibits superelastic properties and increased flexibility over conventional stainless steel which may ease the insertion of the guide wire 15 through the drive shaft lumen 19, including the pre-curved section 100 during placement of the abrasive section 28 proximate the target stenosis.

Examples of superelastic metal alloys, including Nitinol, which are usable to form certain embodiments of the pre-curved section 100 of the present invention are described in detail in U.S. Pat. No. 4,665,906. The disclosure of U.S. Pat. No. 4,665,906 is expressly incorporated herein by reference insofar as it describes the compositions, properties, chemistries, and behavior of specific metal alloys which are superelastic within the temperature range at which the pre-curved section 100 of the drive shaft 20 of the present invention operates, any and all of which superelastic metal alloys may be usable to form the pre-curved section 100 of the drive shaft 20.

Regardless of the method and/or materials used to achieve the pre-curved section 100 of the present invention, pre-curved section 100 is provided in its pre-curved configuration with curved profile as described above prior to insertion into patient's vasculature. The pre-curved section 100 may then mechanically deformed to a generally linear and/or straight configuration and profile. Such straightening deformation may comprise moving the pre-curved section 100 within outer catheter 13. Alternatively, the pre-curved section 100 may be rotated to provide engagement with spanning section of inner tube. This engagement tends to deform, i.e., straighten, the pre-curved section 100 until drive shaft 20 is rotated to disengage pre-curved section 100 and spanning section, thus allowing pre-curved section to return to its pre-curved profile.

Moreover, depending on the operation mode employed, as described below, dynamic adaptability and control of the curvilinear profile by manipulating, e.g., height H and length L, of pre-curved section 100 may be employed by, e.g., thermally inducing the pre-curved section 100 embodiment comprising a shape memory allow such as Nitinol, to cause it to return to its original configuration (either the maximum height H and length L, or varying lengths of H and L).

Thus, one example of operator control over the pre-curved section's 100 curvilinear profile, e.g., height H and length L parameters may be achieved by application of a controlled amount of thermal (or cooling) energy to the pre-curved section 100 which, in this embodiment, comprises a shape memory alloy such as Nitinol. In such an arrangement, the curvilinear profile of the pre-curved section may be made to be more flat, i.e., a smaller height H parameter by cooling the pre-curved section 100. Alternatively, the curvilinear profile may be made to have a greater height H by adding thermal energy to the pre-curved section 100.

Thus, the operator may apply heat to the pre-curved section 100 by bathing the pre-curved section 100 in a heated and/or heat-controlled (heatable and/or coolable) physiologically compatible fluid (e.g., saline, Ringer's Solution, etc.) that is introduced via the lumen of guide catheter 13 as illustrated in FIGS. 1, 7 and 9, through which the drive shaft 20 is introduced. By controlling the temperature of the fluid introduced, either warming or cooling, the temperature of the pre-curved section 100 is similarly controlled such that when guide wire 15 is proximally withdrawn beyond the pre-curved section 100, the curvilinear profile is proportionally and controllingly affected. This allows further dynamic and adaptable control of the pre-curved section's 100 curvilinear profile, e.g., height H and length L, to a plurality of curvilinear profiles to match the vascular environment without requiring the operator to remove the device mid-procedure.

Alternatively, operator control over the shape memory alloy pre-curved section 100 height H and length L parameters to dynamically adapt the pre-curved section 100 to a variety of curvilinear profiles may be achieved by controlling the temperature of the pre-curved section 100 by passing current through the guide wire 15 from its proximal end and then removing the guide wire 15 proximally to allow the pre-curved section 100 to controllably achieve its pre-curved configuration and profile with height H and length L proportional to the heat generated in pre-curved section by the current applied as described. Alternatively, a cooling effect may be realized by using a Peltier device as is well known in the art. As those skilled in the art will recognize, the application of electrical current to pre-curved section 100 may be accomplished by attaching one or two leads operatively connected with pre-curved section 100.

Moreover, operator control over the curvilinear profile, including but not limited to the radial expansion, i.e., H, of pre-curved section 100 and abrasive section(s) comprising grinding and/or cutting elements may be achieved by mechanical means. For example, distal section 52 of drive shaft 20 may be slidable with respect to proximal section 50 of drive shaft 20. Alternatively, proximal section 50 may be slidable with respect to distal section 52 of drive shaft 20. In either case, spanning section 54 may be slidingly received within proximal section 50 and/or distal section 52, thus shortening the length of spanning section 52 and effectively decreasing the curvilinear characteristics, i.e., H and L of pre-curved section 100 in certain embodiments. Alternative embodiments for operator control of curvilinear profile characteristics H and L of pre-curved section 100 may comprise moving proximal section 50 and distal section 52 of the drive shaft closer together or further apart using operator-provided force or alternate mechanisms, e.g., magnetic attraction and/or repulsion between the proximal section 50 and distal section 52. Still more alternatively, operator may pull/retract and/or push/extend drive shaft 20 within catheter 13, thereby exposing more or less of pre-curved section 100 adjacent spanning section 54. Still more alternatively, a wire may be connected to distal section 52 of drive shaft which, if pulled proximally by operator, causes distal section 52 to move proximally and spanning section 54 to be slidingly received within proximal section of drive shaft, thereby decreasing the distance between proximate section 50 and distal section 52. Additional equivalent embodiments for operator-controlled manipulation of the curvilinear profile characteristics H and L of pre-curved section 100 may be readily recognized by the skilled artisan; each such alternative is within the scope of the present invention.

Returning now to FIGS. 4 and 5, one embodiment of the present invention is illustrated in deformed, i.e., straightened profile and in pre-curved undeformed profile. Straightening deformation is accomplished by enclosing precurved section 100 within outer catheter 13 in this embodiment. Further, a concentric abrasive crown 28A is attached to drive shaft substantially at peak P of pre-curved section for directional ablation thereby. Proximally moving catheter 13 and/or distally moving drive shaft 20 frees precurved section 100 from the confines of catheter 13, thus allowing pre-curved section 100 to return to its curvelinear profile. Guide wire 15 is illustrated as disposed within outer catheter 13, but external to drive shaft 20.

FIGS. 6 and 7 illustrate similar principles as the embodiment of FIGS. 4 and 5, except that the abrasive element 28 comprises an external abrasive surface, either a roughened surface or abrasive coating directly on the wire turns of the drive shaft 20.

Another embodiment of the present invention is shown in FIG. 8 with abrasive section 28 comprising an at least partially hollow solid eccentric crown 28B attached to drive shaft 20 as described in connection with FIG. 2 supra. Pre-curved section 100 is provided with height H and length L and formed on the drive shaft 20 proximal to distal portion of drive shaft $20_d$. This embodiment of the present invention is illustrated without straightening deformation(s) discussed supra, thus the illustrated embodiment retains its original pre-curved configuration and profile.

FIG. 9 illustrates yet another embodiment of the present invention with abrasive section 28 comprising an eccentric enlarged section of drive shaft 28C as described supra in connection with FIG. 3. Thus, pre-curved section 100 is provided with height H and length L and is formed on drive shaft 20 proximal to distal portion of drive shaft $20_d$. FIG. 9 illustrates the pre-curved section 100 in its original curved configuration and profile, without straightening deformation(s) discussed supra. The pre-curved section 100 of the present invention thus, comprises a material operating within the material's yield stress and elastic limit and, thus, will have a preformed curved shape that is adaptable to essentially any inner open space of a generally tubular or duct-like lumen.

The pre-curved section 100 of the drive shaft 20 is thus capable of being elastically (but not plastically) deformed in order to substantially straighten in response to straightening deformation structures and methods described herein. The pre-curved section 100 of the drive shaft is, therefore, capable of recovering its original curved configuration and profile, and variations thereof, inside the passageway of the stenosis when the straightening deformation structures and/or methods of the present invention are at least partially removed.

When the pre-curved section 100 of the present invention is at least partially deployed, wherein the at least one abrasive section 28 is radially biased away from its deformed straightened position within a stenosis, the abrasive section 28 may be guided to the location of the lumen requiring ablative attention. This may be achieved by well-known techniques such as inclusion of radiopaque bands and/or markers proximate the abrasive section 28 to allow the operator to locate and position the device. When positioned, the drive shaft 20 may be rotated. This causes abrasive section 28 to spin and/or rotate around, e.g., axis of rotation AR when abrasive section 28 is positioned or located at peak P, either concentrically, i.e., with a rotational diameter substantially equivalent with the abrasive element's resting diameter, and/or eccentrically, i.e., with a rotational diameter larger than the abrasive element's resting diameter resulting in some cases in orbital motion of abrasive section 28. In this manner, the target tissue is ablated while leaving other non-target tissue unharmed.

As described supra, bi-directional rotation of abrasive section 28, alternately engaging grinding and cutting elements comprises various embodiments of the present invention. Moreover, the present invention may comprise at least one abrasive section 28 located at least one position within pre-curved section 100. Thus, the at least one abrasive section 28 may comprise various combinations of abrasive grit size, abrasive element(s), cutting element(s) located within pre-curved section 100 as will be readily understood by the skilled artisan. For exemplary purposes only and without limitation, an abrasive section 100 comprising a cutting element may be provided on the leading (distal) section LS of pre-curved section followed by an abrasive section comprising a coating of abrasive material thereon and disposed at pre-curved section peak P. Still more alternatively, various abrasive sections may be disposed along pre-curved section, along at least one of the more than one axis of rotation, e.g., AR, $AR_{LS}$ and/or $AR_{DS}$, of pre-curved section 100, each having varying grinding and/or cutting characteristics, and wherein the operator may utilize the various straightening deformation structure(s) and/or method(s) described herein to allow engagement of one or more of the at least one abrasive sections provided on pre-curved section to optimize ablation. In addition, as discussed herein, the drive shaft may be rotated in two directions, resulting in additional options for grinding and/or cutting.

Thus, a method of directionally clearing target tissue comprising a stenosis within a lumen using the present invention may comprise:

providing an outer catheter having an outer diameter smaller than the lumen providing a flexible elongated, rotatable drive shaft with a pre-curved section comprising at least one abrasive section thereon;

advancing the drive shaft through lumen of outer catheter;

deforming the pre-curved section of the drive shaft into a substantially linear profile;

advancing the drive shaft into the lumen, e.g., a patient's vasculature to a position proximal the target tissue;

retracting the catheter proximally;

allowing the pre-curved section to move back into its undeformed and curvilinear profile form;

rotating the drive shaft wherein the abrasive section is applied directly to the target tissue;

directionally ablating the target tissue while avoiding other non-target tissue within the lumen;

deforming the pre-curved section by, e.g., reinserting the pre-curved section within the catheter, and substantially straightening the pre-curved section in preparation for withdrawal from the lumen, e.g., the patient's vasculature; and withdrawing the substantially straightened drive shaft from the lumen.

Alternate embodiments may comprise providing dynamic adaptable operator control of the curvilinear profile of the pre-curved section by enabling the operator to (1) controllably apply current to controllingly heat the pre-curved section comprising, e.g., a shape memory alloy such as Nitinol, to induce curving of the pre-curved section; and/or (2) perfuse a heated biocompatible solution, e.g., saline or ringer's solution, through a catheter advanced over drive shaft and pre-curved section, comprising a shape memory alloy such as Nitinol, to induce curving of pre-curved section; and/or (3) perfuse a cooling biocompatible solution to reduce curving of pre-curved section; and/or (4) engage a cooling Peltier device operatively connected to pre-curved section to reduce curving of pre-curved section.

The present invention should not be considered limited to the particular examples described above, but rather should be understood to cover all aspects of the invention. Various modifications, equivalent processes, as well as numerous structures to which the present invention may be applicable will be readily apparent to those of skill in the art to which the present invention is directed upon review of the present specification.

What is claimed is:

1. A directional rotational atherectomy device for directional ablation of target tissue in a blood vessel having a given diameter, comprising:

a guide wire;

a catheter having an outer diameter less than the diameter of the blood vessel and a lumen therethrough;

a flexible elongated, rotatable drive shaft having a lumen therethrough and advanceable over the guide wire and wherein the drive shaft is advanceable within the catheter lumen, the drive shaft comprising wire turns, a pre-curved section comprising an undeformed curvilinear profile that is pre-formed and pre-shaped during manufacture of the drive shaft, wherein the undeformed curvilinear profile of the pre-curved section is achieved whenever the pre-curved section is unrestrained and a distal section operatively connected to a bearing configured to allow the drive shaft to rotate thereby, and wherein the pre-curved section is deformable to a substantially straightened profile when advanced over the guide wire and, when not advanced over the guide wire, the pre-curved section comprises the undeformed curvilinear profile;

the drive shaft further comprising:
  a resting diameter corresponding with the deformed and substantially straightened pre-curved section,
  an axis of rotation corresponding with the deformed and substantially straightened pre-curved section, and
  a swept diameter achieved during high-speed rotation of the undeformed pre-curved section of the drive shaft which is larger than the resting diameter;

an inner tube advanceable within the lumen of the catheter, the inner tube comprising a proximal section, a distal section and a spanning section therebetween, the proximal section and distal section having a lumen therethrough, the bearing disposed in the distal section and wherein the drive shaft is rotatable in the lumen of the proximal and distal section, the spanning section further comprising a variable length controllable by an operator; and at least one eccentric abrading crown attached to the drive shaft at the pre-curved section, the at least one eccentric abrading crown comprising a center of mass that is radially offset from the rotational axis of the drive shaft when the drive shaft comprises the deformed substantially straightened profile.

2. The rotational atherectomy device of claim 1, the pre-curved section further comprising a variable height and a variable length, controllable by an operator.

3. The rotational atherectomy device of claim 2, wherein the pre-curved section comprises a leading section, a distal section, and a peak therebetween, and wherein at least one at least one eccentric abrading crown is operatively connected to the leading section, the distal section and/or the peak therebetween.

4. The rotational atherectomy device of claim 1, wherein the pre-curved section further comprises at least one radiused section.

5. The rotational atherectomy device of claim 1, wherein the pre-curved section further comprises two radiused sections.

6. The rotational atherectomy device of claim 5, further comprising the two radiused sections each comprising a curvature, and wherein the curvatures of the two radiused sections are substantially equal.

7. The rotational atherectomy device of claim 5, further comprising the two radiused sections each comprising a curvature, and wherein the curvatures of the two radiused sections are not substantially equal.

8. The rotational atherectomy device of claim 1, wherein the pre-curved section further comprises a peak.

9. The rotational atherectomy device of claim 8, wherein the at least one eccentric abrading crown is at least partly disposed on the peak.

10. The rotational atherectomy device of claim 1, wherein the drive shaft comprises a distal end and wherein pre-curved section is disposed proximate the distal end of the drive shaft.

11. The rotational atherectomy device of claim 1, further comprising the pre-curved section being formed of a shape memory alloy.

12. The high-speed rotational atherectomy system of claim 11, further comprising:

a fluid supply line operatively connected to the catheter; and a biocompatible solution that is of a controlled temperature, wherein the
biocompatible solution is urged through fluid supply line and into the catheter to
provide operator control over the shape of the curvilinear profile.

13. The rotational atherectomy device of claim 1, further comprising the pre-curved section being formed of Nitinol.

14. The rotational atherectomy device of claim 1, further comprising the pre-curved section being adapted to a certain curvilinear profile.

15. The rotational atherectomy device of claim 14, further comprising the pre-curved section being dynamically adaptable to a plurality of curvilinear profiles.

16. The rotational atherectomy device of claim 1, wherein the drive shaft is capable of rotating in two opposing directions and wherein the at least one eccentric abrading crown ablates less in one rotational direction and ablates more in the opposing rotational direction.

17. The rotational atherectomy device of claim 16, wherein the at least one eccentric abrading crown further comprises a grinding element on one side and a cutting element on an opposing side, wherein the drive shaft is capable of rotation in two directions and wherein rotation in one direction engages the grinding element with target tissue and rotation in the other direction engages the cutting element with target tissue.

18. The directional rotational atherectomy device of claim 1, wherein the pre-curved section is deformed by mechanical deformation.

19. The directional rotational device of claim 18, wherein the pre-curved section comprises a shape memory alloy and the deformation comprises cooling the pre-curved section.

20. The directional rotational device of claim 1, further comprising operator control over the curvilinear profile of the pre-curved section, by varying the length of the spanning section.

* * * * *